United States Patent [19]

Ross, Jr.

[11] Patent Number: 4,775,780
[45] Date of Patent: * Oct. 4, 1988

[54] BLOOD ALCOHOL INDICATOR

[76] Inventor: John R. Ross, Jr., 13020 Long Boat Way, Del Mar, Calif. 92014

[*] Notice: The portion of the term of this patent subsequent to Dec. 23, 2003 has been disclaimed.

[21] Appl. No.: 945,352

[22] Filed: Dec. 23, 1986

Related U.S. Application Data

[63] Continuation-in-part of Ser. No. 781,017, Dec. 23, 1986, Pat. No. 4,631,393.

[51] Int. Cl.$^4$ ................................. G06C 3/00
[52] U.S. Cl. ..................... 235/89 A; 422/84; 235/1 R; 235/90
[58] Field of Search ................. 177/190–200; 422/84; 436/132; 235/89 A, 65, 87 A, 123, 124, 127, 1 R

[56] References Cited

U.S. PATENT DOCUMENTS

| 227,050 | 3/1880 | Palmer | 177/200 |
| 1,354,275 | 9/1920 | Bachman | 177/200 X |
| 1,869,723 | 8/1932 | Van Duyn | 177/200 X |
| 4,631,393 | 12/1986 | Ross | 235/89 A |

FOREIGN PATENT DOCUMENTS

| 77671 | 3/1894 | Fed. Rep. of Germany . | |
| 977162 | 3/1951 | France | 177/199 |
| 316742 | 3/1930 | United Kingdom | 177/199 |

Primary Examiner—Barry S. Richman
Assistant Examiner—Michael S. Gzybowski

[57] ABSTRACT

Alcohol pieces representing alcohol consumed are placed on one side of a balance board supported by as support structure. A time piece (or pieces) representing the alcohol oxidized by the body in a period of time is placed on the other side of the balance board and the tilt of the board tells the drinker what his or her blood alcohol level is.

7 Claims, 4 Drawing Sheets

BLOOD ALCOHOL INDICATOR

This application is a continuation-in-part of patent application Ser. No. 781,017 scheduled to issue as U.S. Pat. No. 4,631,393 on Dec. 23, 1986.

My invention relates to devices for measuring or estimating blood alcohol levels.

BACKGROUND OF THE INVENTION

Thousands of people are killed in the United States each year by drunk drivers. Many of these people would not have been driving had they realized they had drunk too much. Drunk drivers are having to spend time in jail and pay fines in the range of $1,000 because they did not know they had drunk too much. On the other hand, alcohol in moderation may be good for you. Studies have indicated that a glass of wine a day can increase your lifespan. Cocktail parties are a part of the American way of life. It would be nice if people who drink would not drive, but that is too much to hope for. Very often there is no practical way to get home from a party or the bar except to drive. We need a device to tell us when we have had enough so we can stop or slow down. It should be cheap enough so one could be in every bar and every home where liquor is served. It should be easy to operate, so moderately intoxicated people could operate it and understand the results. Devices exist for estimating blood alcohol level from urine samples, breath samples and blood samples. These devices are too expensive for universal use. Charts exist which can be used to estimate blood alcohol level. These charts are free but they are not doing the job. Why, I do not know. Maybe people don't believe them. Maybe many people can't understand the charts.

SUMMARY OF THE INVENTION

My invention is a simple blood alcohol estimating device. Alcohol pieces representing alcohol consumed are placed on one side of a balance board supported by a support structure. A time piece (or pieces) representing the alcohol oxidized by the body in a period of time is placed on the other side of the balance board and the tilt of the board tells the drinker what his or her blood alcohol level is.

DETAILED DESCRIPTION OF THE PREFERRED EMBODIMENT

Figure 1:
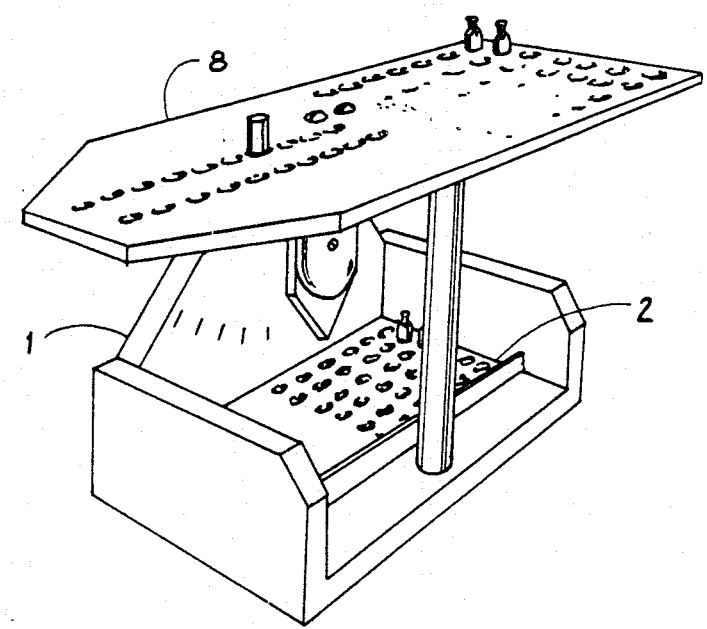
FIG. 1. is a pictorial view of a preferred embodiment of my invention.

A preferred embodiment of my invention can be described by reference to the figures. The support structure 1 is made of wood. Its functions are to support a balance board 8, provide a rack 2 for holding the alcohol peices 22 and the time peices 20 when these pieces are not being used on the balance board and as a mount for the scale 3. Mounted in slots 16 at the top of back support 4 and the front support 5 is a support beam 6 made of brass. At two places on the support beam, knife edges 7 have been ground.

Balance board 8 is made of a hardwood board 6"×11"×¼". Ballance board 8 is divided at a center line 30 which passes over the center of gravity of balance board 8 and defines two sides of the board. On a first side, seven rows of holes slightly larger than 5/16" are drilled, each row comprising seven holes. The rows are located so that one set of alcohol pieces can be used to indicate alcohol blood levels for persons having a wide range of weights, especially 100 pounds, 125 pounds, 150 pounds, 175 pounds, 200 pounds, 250 pounds and 300 pounds. My preferred embodiment basically reproduces the information set forth in the table published by the Automobile Club of Southern California in a phamplet entitled "None For the Road, A Guide to California's DUI Laws", Phamplet No. 60442 1-85:

|  | BLOOD ALCOHOL LEVEL | | |
| --- | --- | --- | --- |
|  | Body Weight in Pounds | | |
| # of Drinks* | 100 | 160 | 200 |
| 1 | .04% | .02% | .02% |
| 2 | .08% | .05% | .04% |
| 3 | .11% | .07% | .06% |
| 4 | .15% | .09% | .08% |
| 5 | .19% | .12% | .09% |
| 6 | .23% | .14% | .11% |

The 100 pound row is located 5" from the center line 30. This establishes the location of the other rows in accordance with the following table:

| WEIGHT <pounds> | DISTANCE FROM CENTER LINE <inches> |
| --- | --- |
| 100 | 5 |
| 125 | 4 |
| 150 | 3.33 |
| 175 | 2.86 |
| 200 | 2.5 |
| 250 | 2 |
| 300 | 1.67 |

Of course, other rows could be added. The rows should be positioned so that the product of distance and the weight equals 500 inches-pounds.

Figure 5:
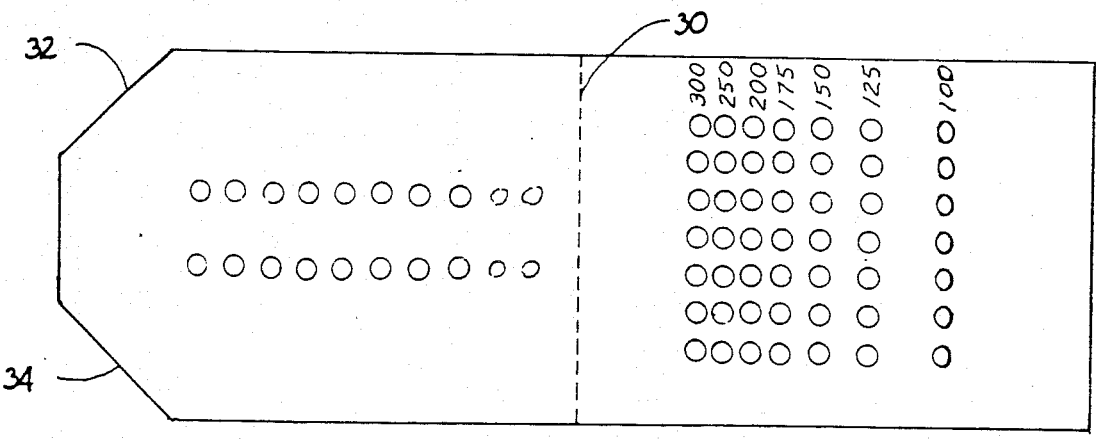
FIG. 5. is a top view of the balance board portion of the above embodiment.

On a second side of balance board 8, two columns af holes slightly larger than 5/16" are provided as shown in FIG. 5 each column containing 10 holes the centers of which are spaced at ½" intervals the last two holes being spaced 5" from the center line. Balance board 8 is trimmed at 32 and 34 so that the board balances along center line 30.

Two ¼"×¼"×150 " pivot blocks 11 are glued to the bottom of the balance board along the center line 30. The pivot blocks are made of brass and comprise an inverse "V" 12 cut into the bottom of the pivot blocks along center line 30. The pivot blocks are located so that the inverse "V" will fit above the two knife edges of the support beam 6.

Figure 4:
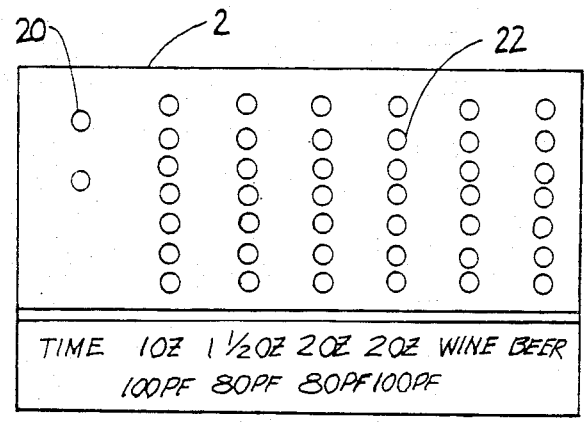
FIG. 4. is a top view of the rack portion of the above embodiment.

FIG. 4 is a top view of rack 2. On this rack are spaces for six sets of alcohol pieces 22. The alcohol pieces represent six typical alcoholic drinks as set forth below along with the alcohol content and the weights of the pieces.

| DRINK | ALCOHOL WEIGHT <oz> | PIECE WEIGHT <gm> |
|---|---|---|
| 12 oz bottle of beer | 0.5 | 3.25 |
| 4 oz glass of table wine | 0.5 | 3.25 |
| 2 oz 100 proof whiskey | 1.0 | 7.00 |
| 2 oz 80 proof whiskey, gin or vodka | 0.8 | 5.60 |
| 1½ oz 80 proof brandy | 0.6 | 4.20 |
| 1 oz 100 proof whiskey, gin or vodka | 0.5 | 3.25 |

Figure 6:
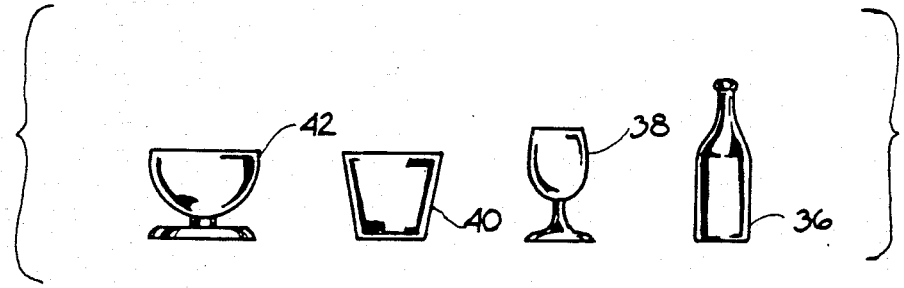
FIG. 6. is a view of some alcohol pieces.

As can be seen the piece weight is proportional to the alcohol content of the drink. The pieces are generally cylindrical made from 5/16" diameter rods of various materials. The pieces preferably are cut in shapes of containers in which the drinks are typically served as shown in FIG. 6. The beer piece 36 is made of wood, wine 38 is made of aluminum, wiskey, gin and vodka 40 is made of brass and the brandy sniffer 42 is also made of brass.

Figures 2, 3:
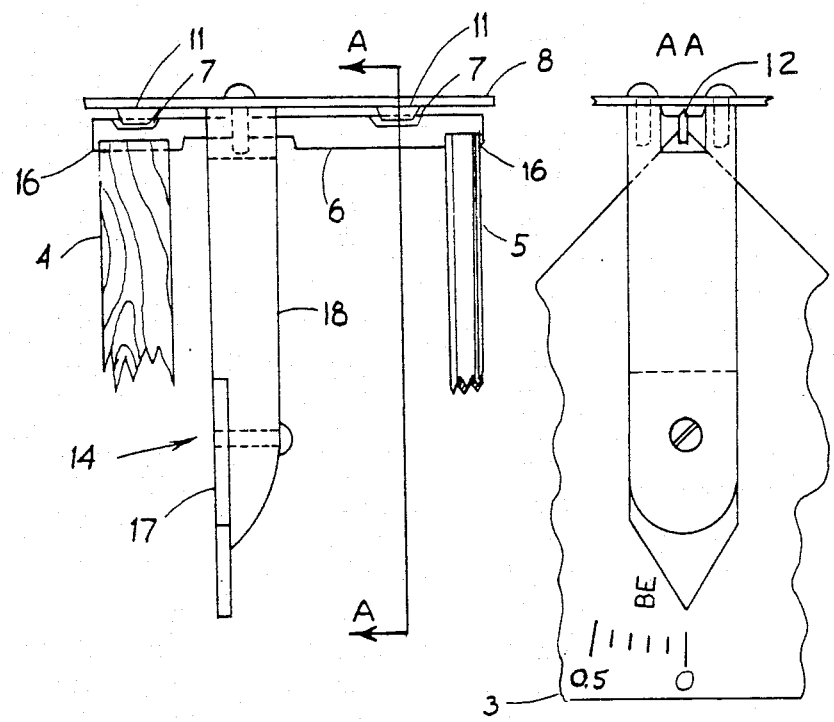
FIG. 2. is a side view of a portion of the above embodiment.
FIG. 3. is a cutaway view of a portion of the above embodiment.
Figure 7:
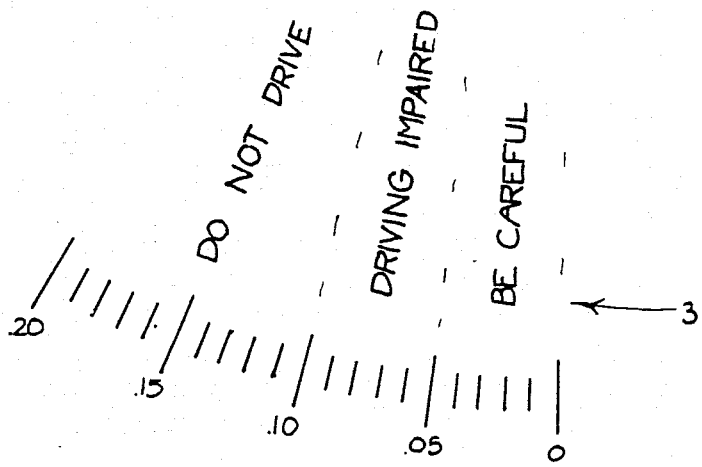
FIG. 7. is a blowup of the scale portion of the above embodiment.

A pointer 14 is attached to balance board 8 at center line 30 as shown in FIG. 2 and FIG. 3. The pointer 14 is comprised of wooden arm 18 and brass head 17, the size of the brass head is chozen to provide the proper degree of tilt for balance board 8 with a given torque differential applied by alcohol pieces and time pieces placed on balance board 8. The heavier the head the smaller the tilt for a given differential. Preferably, the pointer is set at least ⅓ the length of the balance board. A scale 44 is disposed on support 1 as shown in FIG. 1. The scale is blown up in FIG. 7. The scale can be developed and calibrated by placing 3.25 gram alcohol pieces (1 oz 100 proof liquor) at various locations on the balance board and marking the scale in percent blood alcohol level so that it reads the appropriate level. For example, four of these 3.25 gram peices in the 100 pound row must give a blood alcohol level of 0.15% in accordance with the above table. Therefore, the scale is marked as 0.15% at the place where pointer 14 is pointing. Simularly three 3.25 gram pieces gives me a mark for 0.11% two gives 0.08%, one gives 0.04% and zero gives 0.00%. Five gives 0.19% and so forth. The scale can be checked by placing the 1 oz peices in other rows. For example, four one oz pieces in the 200 pound row should give a blood alcohol level of 0.08%.

For my preferred embodiment two time pieces 20 are provided. Each weighs 13 grams and they are properly labled to distinguish them as time pieces. The time pieces are used to indicate how much the blood alcohol level has been reduced because of the oxidation of the alcohol by the body. Typically, a healthy person will oxidize alcohol so as to reduce his or her percent blood alcohol at the rate of about 0.015% for each hour measured from the start of consumption. Thus, ten hours after the start of drinking oxidation would reduce the level by 0.15%. As indicated above, a 100 pound person consuming four 1 oz 100 proof drinks will have a blood alcohol level of 0.15%. After ten hours this alcohol would be oxidized away. On my blood alcohol indicator this is demonstrated by placing one of the time pieces in one of the ten hour locations (at five inches from the center line). This exactly balances the four 3.25 gram alcohol pieces at five inches from the center line on the other side. At five hours the time piece would be in the five hour location and the point would point to between 0.07% and 0.08%. Twelve hours would be represented by one time piece in a ten hour location and one time piece in a two hour location.

To operate the board, the drinker merely places alcohol pieces representing the drinks he or she has consumed in locations corresponding to his or her weight. The drinker also places a time piece in the time location corresponding to the time since he or she started drinking. Pointer 14 will point to his or her blood alcohol level. The drinker will have a good indication of how risky it would be to drive. By moving the time piece the drinker can see how much time it would take for his or her blood alcohol level to decrease to a safer level. A drinker producing a 0.11% level may decide that a little four hour nap (0.06%) is appropriate.

The foregoing description of the present invention has been presented for the purpose of illustration and is not intended to limit the invention to the precise form disclosed. It is, therefore, to be understood that within the scope of the appended claims, the invention may be practiced othewise than specifically described.

I claim:

1. A blood alcohol estimating device comprising:
   a support structure
   a plurality of alcohol pieces, each of said alcohol pieces comprised of solid matter and constructed so as to be identified as representing a quantity of alcohol consumed in different drinks and having a weight approximately proportional to the mass of alcohol in each of the drinks,
   at least one time piece representing a quantity of alcohol oxidized in a human body over a specific period of time and having a weight approximately proportional to the mass of said oxidized quantity of alcohol,
   a balance board supported by said support structure along a line on said balance board defining a center line, said center line defining two sides of said balance board, said balance board having a plurality of locating means for easy placement and removal of said alcohol pieces on one side and for easy placement and removal of said at least one time piece on the other side thereof,
   a scale means disposed on said support structure to indicate blood alcohol level or other measurement of intoxication and,
   a pointer means disposed on said balance board and cooperating with said scale means for indicating degrees of intoxication,
   said scale means, said alcohol pieces, said at least one time piece, said locating means and said pointer means being sized and arranged so that when selected ones of said alcohol and time pieces are placed at appropriate ones of said locating means, a person's approximate blood alcohol level or other measure of intoxication can be read from said scale means based on the tilt of said balance board.

2. A blood alcohol estimating device in accordance with claim 1 wherein said alcohol pieces comprise at least three sets of alcohol pieces, each set comprising a plurality of alcohol pieces wherein each of the alcohol pieces of each set is constructed so as to be identified as representing a quantity of alcohol contained in different alcoholic drinks and each alcohol piece has a weight approximately proportional to the mass of alcohol contained in each of the alcoholic drinks.

3. A blood alcohol estimating device in accordance with claim 1 wherein said scale means is graduated in percent blood alcohol level.

4. A device in accordance with claim 1 wherein said locating means for placement of said alcohol pieces are arranged in rows, each row having means designating it as representing a person having a specific body weight, a row representing lighter persons being farthest from said center line and a row representing heaver persons being closest to said center line.

5. A device in accordance with claim 1 wherein said locating means for easy placement and removal of said at leat one time piece are arranged so that said at least one time piece can be placed in or on various ones of said locating means to indicate on said scale means alcohol oxidized during various time increments.

6. A device in accordance with claim 1 wherein the pointer means comprises a pointer arm having a length at least ⅓ the length of the longest dimension of the balance board.

7. A device in accordance with claim 6 wherein said pointer means also comprises a tip piece made of a material substantially heaver than the rest of the pointer arm.

* * * * *